United States Patent [19]

Toma et al.

[11] Patent Number: 5,044,378
[45] Date of Patent: Sep. 3, 1991

[54] DEVICE FOR DISTRACTING PATIENTS DURING INTRAVENOUS INJECTIONS

[75] Inventors: Beatrice Toma, London, Canada; John Toma, Brooklyn, N.Y.; Rita Toma, Guelph, Canada; Lorraine Toma-Jones, Mississauga, Canada; Thomas Toma, Blenheim, Canada; Kathy Ducharme, Windsor, Canada; Yvonne Toma, Culver City, Calif.

[73] Assignee: Jeibralt Incorporated, London, Canada

[21] Appl. No.: 572,779

[22] Filed: Aug. 27, 1990

[51] Int. Cl.⁵ .............................................. A61F 5/37
[52] U.S. Cl. ..................................... 128/877; 128/878
[58] Field of Search ............... 128/878, 877, 845, 846, 128/849, 851, 869; 446/268, 304

[56] References Cited

U.S. PATENT DOCUMENTS 3,986,505 10/1976 Power .................................. 128/854

Primary Examiner—Robert A. Hafer
Assistant Examiner—David J. Kenealy

[57] ABSTRACT

A portable medical unit that is used during the medical procedures of extracting blood from and giving needles to children. The unit provides a concealed work area with storage pockets; a vinyl cushion arm rest; and straps to retain the child's arm during the above noted procedures. The unit features distraction elements such as a painted clown's face and an opening through the mouth where the child inserts his/her arm. When not in use, the work area remains concealed with a flap that opens only when the child's arm is inserted into the mouth. Also featured is the clown's hair which is made of synthetic material, is brightly colored, and offers a tactile distraction. The nose of the clown connects to a pumping system which, when the child squeezes inflates a balloon that is connected to the pumping system by a tube. The balloon can be removed and given to the child as a reward for good behavior. When open the two forms are secured in place by locking hinges. When closed the unit is retained shut by clasps and carried by a handle. The unit can be rested on a table in a hospital, a clinic, a child's home, or a doctor's office for easy use.

3 Claims, 3 Drawing Sheets

DEVICE FOR DISTRACTING PATIENTS DURING INTRAVENOUS INJECTIONS

BRIEF SUMMARY OF INVENTION

A unit that is used to distract children while medical practitioners take blood from or give them needles. The unit is portable, opening and closing like a carrying case. The outer front of the case is a clown's face; the mouth is hollow covered only by a "flap" on the interior side. The rest of the face is painted onto the durable plastic base, with the exception of the hair and nose.

The nose of the clown is a rubber pump that pushes air (when the child squeezes it) up a tube that is located on the interior side or behind the clown's face. At the top of the head, and attached to the tube is a balloon. The squeezing of the nose sends air to the balloon, thus inflating it. The balloon can be removed once inflated and given to the child as a reward for good behavior.

The hair is brightly colored and of a synthetic material that the child can touch further distracting him/her during the medical procedures. The hair is attached to the face of the case rather than painted onto it.

The child pushes his/her arm through the mouth of the clown. Behind the clown's face is a work area for the medical practitioner that includes a velcro strap to hold the child's arm in place. There are two small storage pockets on the inside of the case, where a tournaquet and other medical accessories can be kept. The work area is concealed, and can be easily sterilized between uses.

The object of the unit is to distract the child with the large clown's face, the squeezing of the nose which subsequently inflates the balloon, the bright hair, and by concealing the work area for the medical practitioner.

It is an object of this unit to provide the medical practitioner with an area to work concealed from the child, that is easily cleaned and safe for the child.

It is also an object of this unit to provide the medical practitioner with reasonable storage space, safely concealed from the child's perceptions.

It is also an object of this unit to provide the medical practitioner with a device that is portable, easy to assemble and safe to use.

It is also an object of this unit to minimize the trama that some children associate with the medical profession by reducing the frightening experience of having blood taken or needles given.

It is also the object of this unit to provide the child with a reinforcement for good behavior by giving the child the balloon that they have inflated at the end of the procedure.

DESCRIPTION OF THE PREFERRED EMBODIMENTS

Referring now to FIGS. 1-6, there is shown a portable medical unit that comprises two distinct collapsible forms 1, 15. In its closed state 19, the unit is maintained portable by clasps 7 and carried by a handle 18.

Figure 1:
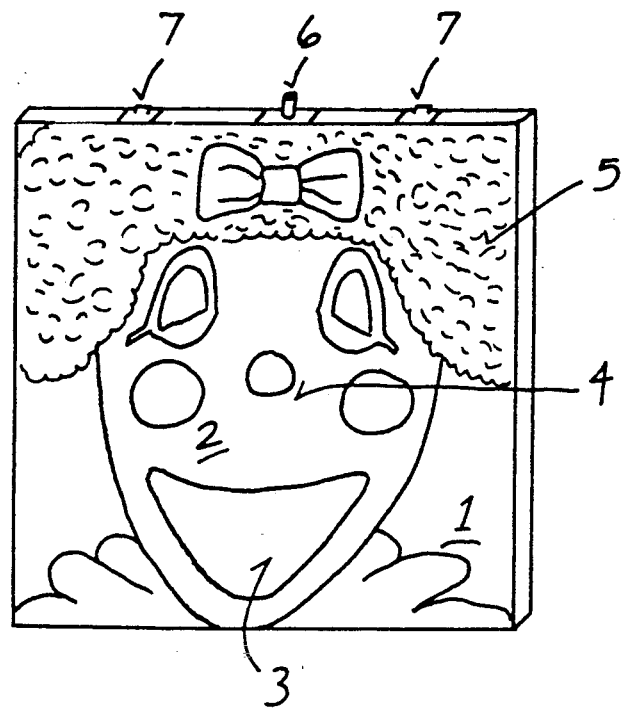
FIG. 1 is a front view of the medical unit as seen by the child.

In its open form the outer side of form 1 as shown in FIG. 1 exposes a clown's face 2. The face itself 2, is painted onto unit 1 with bright colors and having an opening 3. The opening is concealed by a flap 11 (FIG. 2) when not in use. The flap 11 is securely fastened to the opposite side of the form 1a.

Figure 3:
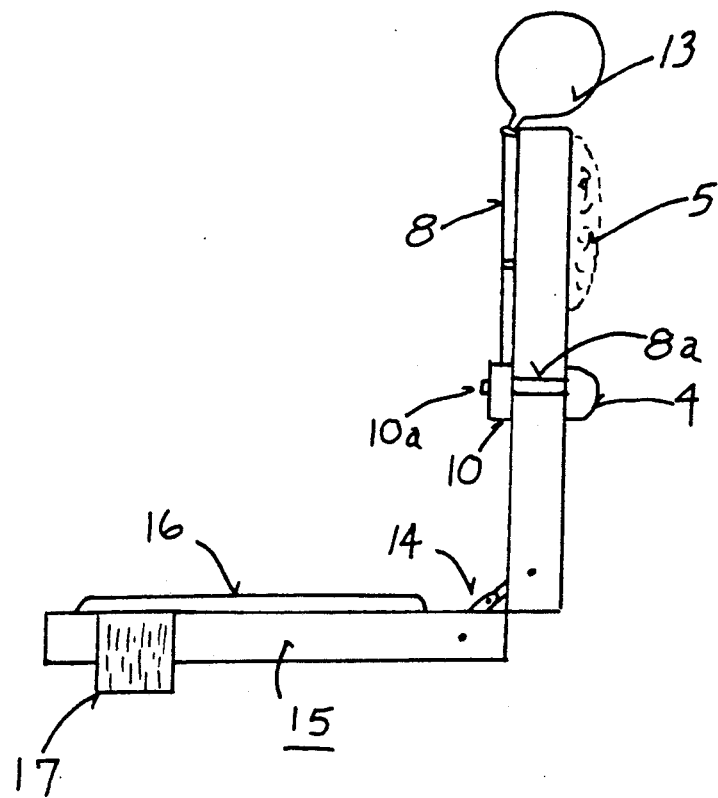
FIG. 3 is a side view of the complete unit when opened and ready for use.
Figure 4:
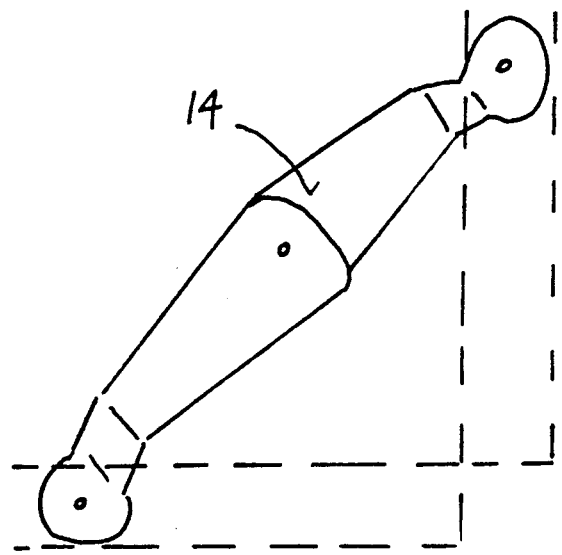
FIG. 4 is an exploded side view of one of the locking hinges that are used to support the unit when open.

FIG. 3 shows the nose of the clown 4 which is made of rubber, connected to a tube 8a that penetrates 1 and connects to a pumping device 10 on the opposite side. When the nose is contracted it pushes air through tube 8a, through the pumping system 10, and up through tube 8 that connects 6 to the balloon 13; thus inflating it. The pumping system 10 has an opening 10a through which air is drawn when the nose is released. Air is drawn back into the nose through opening 10a refilling the nose enabling additional air to be pumped up to the balloon 13 when the nose 4 is further contracted. Contraction of the rubber nose 4 is facilitated by the squeezing motion from the child's hand.

The clown's hair 5 as shown in FIG. 1 is made of a synthetic material and is securely fastened to form 1. It is bright in color, curly, and provides for additional distraction by its tactile attraction.

Figure 2:
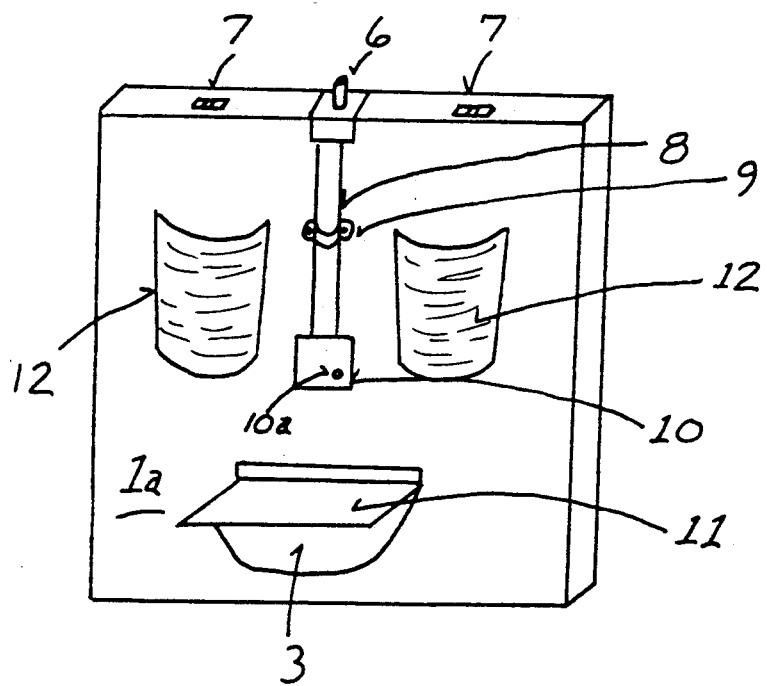
FIG. 2 is the opposite side of the front of the unit when it is opened and ready for use.

The inner side form 1a as shown in FIG. 2 has at least two pocket like storage containers 12 that are securely attached and made of expandable material. The pumping system 10 and the connecting tube 8 are securely fastened with a clamp 9.

Figure 5:
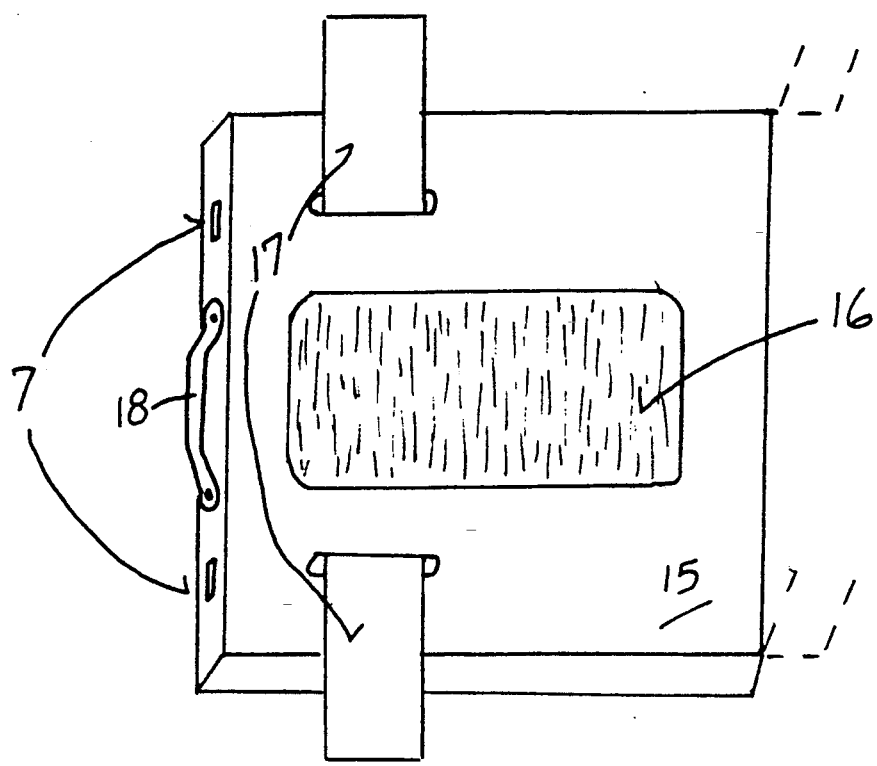
FIG. 5 is a view of the work area as seen by the medical practitioner when the unit is open.

The second form 15 displayed in FIG. 5 has a work area 16, a handle 18, and a set of straps 17 that are all securely fastened to the form. The work area 16 is a cushion that is made of easily cleaned vinyl. The straps 17 are made of material with velcro fasteners that connect them together and can be used to securely strap the child's arm to the cushion 16.

Figure 6:
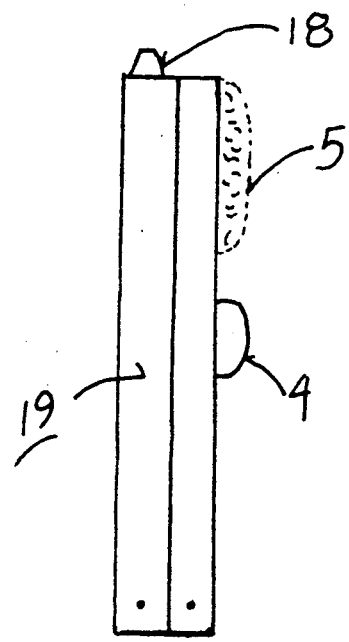
FIG. 6 is a side view of the unit when closed and in its portable state.

Connecting the two forms 1 and 15 are collapsible hinges 14 (shown in FIG. 4) that are securely fastened to the corners of both of the forms. The hinges 14 can be locked when the unit is opened thereby holding it securely in place. When the unit is in its portable state 19 as shown in FIG. 6 the clasps 7 keep the unit securely closed. The unit can be carried with the handle 18.

When ready for use, the unit as shown in FIGS. 1-5 can be placed on the edge of a table in a doctor's office, in a home, a clinic, a laboratory, or in a hospital.

Although this invention has been described in connection with specific forms of embodiments thereof, it will be appreciated that various modifications other than those discussed above may be resorted to without departing from the spirit or scope of the invention. For example, equivalent elements may be substituted for those specifically shown and described. Certain features may be used independently of other features, and in certain cases, particular locations of elements may be altered or interposed all without departing from the spirit or scope of the invention as defined in the claims.

What is claimed is:

1. A portable medical unit that aids during the procedures of the extraction of blood from, and/or the giving of needles to a patient comprising;

a first form and a second form that are joined together at adjacent corners by at least one hinge, said forms having the ability to be collapsed together in which case inside surfaces of the forms will face each other in parallel planes, or retained open in which case the first form shall be situated at an angle to the second form, a hollowed opening through the first form through which a patient may insert his or her arm, the second form having a padded work area attached to its inside surface with strap means for retaining a patient's arm to the work area when arm is placed through the opening in the first form, patient distraction means attached to the exterior side of the first form for distracting a patient during said procedures.

2. The medical unit of claim 1 further comprising;

distraction means including the face of a clown painted on the first form in such a manner that the hollow opening is located at and gives the impression of the clown's mouth in the painting, a plastic pump attached to the first form at the location of and giving the impression of being the clown's nose in the painting with tube means connected to the pump and running to a corner of the first form for attaching a balloon to be pumped up with air, the work area includes at least two pocket storage containers attached to the first or second forms, a flap form attached to the first form in such a manner that it covers said hollow opening and conceals the work area from patient, the work area being easily sterilized between uses, the hinge means including locking means for retaining the unit open, clasps situated at adjacent corners of the separate forms when said forms are collapsed together for locking forms in the collapsed position, a handle attached to the corner of one of said forms for carrying purposes.

3. A method of distracting a patient during the medical procedures of blood extraction or vaccinations comprising the following steps;

a) utilizing a portable medical unit as set forth in claim 1, b) inserting patient's arm through the hollow opening from the exterior side of the first form, c) strapping patient's arm to the padded work area of the second form, d) utilizing; a brightly colored clown's face painted on the exterior side of the first form with suitable decoration to further enhance the clown's features, a flap situated on the inside surface of the first form for concealing the opening and thus the work area when a patient's arm is not inserted, a rubber pump with a tube extending from the pump to simulate the painted clown face's nose, e) distracting patient by allowing patient to squeeze said pump to inflate a balloon attached to the end of the tube, f) administering the medical procedures while the patient is distracted g) detaching the balloon once inflated and giving it to the patient as a reward.

* * * * *